US00PP36436P2

(12) United States Plant Patent
Rietberg

(10) Patent No.: US PP36,436 P2
(45) Date of Patent: Feb. 11, 2025

(54) ***CALLUNA* PLANT NAMED 'Lynn'**

(50) Latin Name: *Calluna vulgaris*
Varietal Denomination: Lynn

(71) Applicant: Henrik Christiaan Cozijn Rietberg, Wezep (NL)

(72) Inventor: Henrik Christiaan Cozijn Rietberg, Wezep (NL)

(73) Assignee: EDENS CREATIONS BV, Wiezep (NL)

( * ) Notice: Subject to any disclaimer, the term of this patent is extended or adjusted under 35 U.S.C. 154(b) by 0 days.

(21) Appl. No.: 18/582,771

(22) Filed: Feb. 21, 2024

(51) Int. Cl.
*A01H 5/02* (2018.01)
*A01H 6/36* (2018.01)

(52) U.S. Cl.
USPC ..... Plt./231

(58) Field of Classification Search
USPC ..... Plt./231
CPC ..... A01H 5/02; A01H 5/00; A01H 6/36
See application file for complete search history.

(56) References Cited

PUBLICATIONS

UPOV Pluto 20240624 for *Calluna* Lynn, retrieved on Jun. 27, 2024 at https://pluto.upov.int/result, one page. (Year: 2024).*

* cited by examiner

*Primary Examiner* — June Hwu
(74) *Attorney, Agent, or Firm* — Penny J. Aguirre

(57) ABSTRACT

A new cultivar of *Calluna* plant named 'Lynn' that is characterized by its highly floriferous blooming habit, its long life span as both an indoor and garden plant, and its flowers that are deep purple in color.

3 Drawing Sheets

Botanical classification: *Calluna vulgaris.*
Variety denomination: 'Lynn'.

CROSS REFERENCE TO RELATED APPLICATIONS

This application is related to a European plant breeders' rights application filed on Jan. 24, 2022, application No. 2022/0205. The information for the plant breeders' rights application was received directly from the Inventor. This application is co-pending with a U.S. Plant Patent Application filed for a plant derived from the same breeding program that is entitled *Calluna* Plant Named 'Viva' (U.S. Plant patent application Ser. No. 18/528,786).

BACKGROUND OF THE INVENTION

The present invention relates to a new and distinct cultivar of *Calluna vulgaris* and will be referred to hereafter by its cultivar name, 'Lynn'. 'Lynn' is a new cultivar of evergreen shrub grown for use as a landscape plant.

The new Invention arose as the result of an ongoing controlled breeding program by the Inventor in Wezep, The Netherlands. The goal of the breeding program is to develop new cultivars of *Calluna* with healthy plant habits and long life spans as both indoor and garden plants that produce numerous flowers in clear colors. 'Lynn' arose from a cross made in September 2014 between unnamed and unpatented proprietary plants from the Inventor's breeding program. The female parent designated by accession No. K12-1163 and the male parent designated by accession No. E13-105. 'Lynn' was selected as a single unique plant by the Inventor in September 2015 from the resulting seedlings of the above cross.

Asexual propagation of the new cultivar was first accomplished by the Inventor by softwood stem cuttings in September of 2015 in Wezep, The Netherlands. Asexual propagation of the new cultivar by softwood and hardwood stem cuttings has determined that the characteristics are stable and are reproduced true to type in successive generations.

SUMMARY OF THE INVENTION

The following traits have been repeatedly observed and represent the characteristics of the new cultivar. These attributes in combination distinguish 'Lynn' as a unique cultivar of *Calluna.*

1. 'Lynn' exhibits a broadly spreading and upright plant habit.
2. 'Lynn' exhibits a highly floriferous blooming habit.
3. 'Lynn' exhibits a long life span as both an indoor and garden plant.
4. 'Lynn' exhibits flowers that are deep purple in color.

The female parent of 'Lynn' differ from 'Lynn' in having a less floriferous blooming habit, flowers that are lighter purple in color, and a shorter life span as an indoor and garden plant. The male parent of 'Lynn' differs from 'Lynn' in having less dense branching, a less floriferous blooming habit, and flowers that are lighter purple in color. 'Lynn' can be most closely compared to the *Calluna* cultivars 'Lianne' (not patented), 'Liset' (not patented), and 'Viva'. 'Lianne' and 'Liset' are both similar to 'Lynn' in foliage and flower color. 'Viva' is similar to 'Lynn' in having a floriferous blooming habit, a similar plant habit, and similar foliage color. 'Lianne' differs from 'Lynn' in having a less upright plant habit, a less floriferous blooming habit, and a shorter life span as an indoor and garden plant. 'Liset' differs from 'Lynn' in having less vigorous growth habit, a less floriferous blooming habit, and a shorter life span as an indoor and garden plant. 'Viva' differs from 'Lynn' in having flowers that are white in color.

BRIEF DESCRIPTION OF THE DRAWINGS

The accompanying color photographs illustrate the overall appearance and distinct characteristics of the new *Calluna*. The photographs were taken of a 1-year-old plant as grown outdoors in a 10-cm container in Wezep, The Netherlands.

The photograph in FIG. 1 provides a side view of the plant habit of 'Lynn' in bloom.

Figure 1:
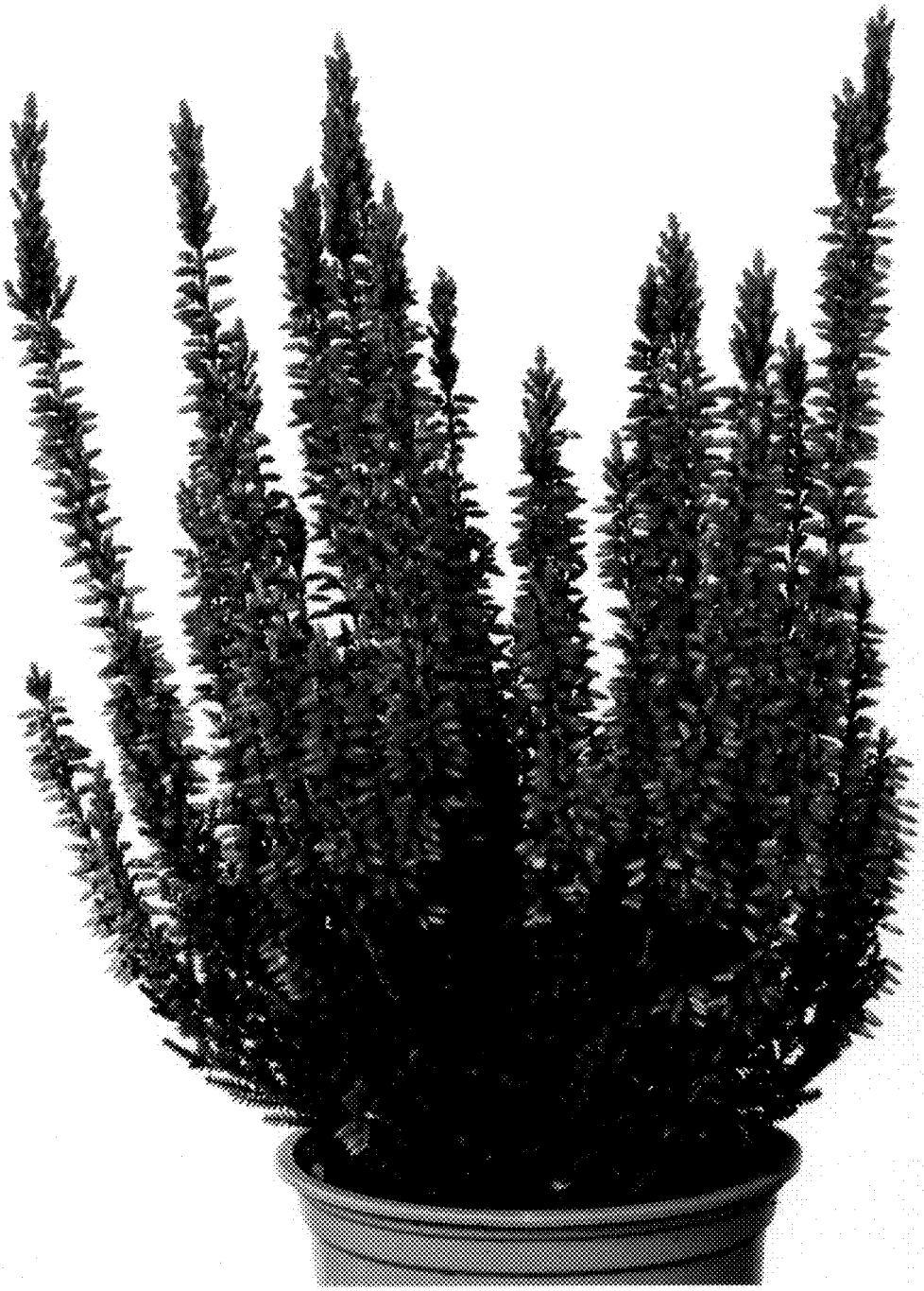
Figure 2:
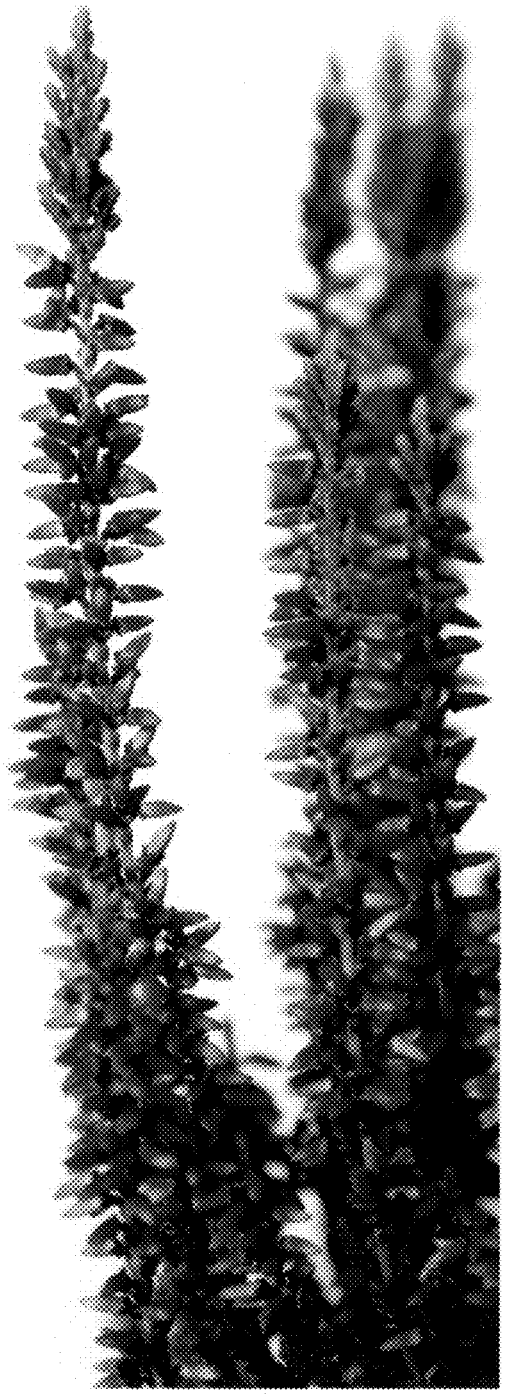

The photograph in FIG. 2 provides a close-up view of the inflorescences of 'Lynn'.

Figure 3:
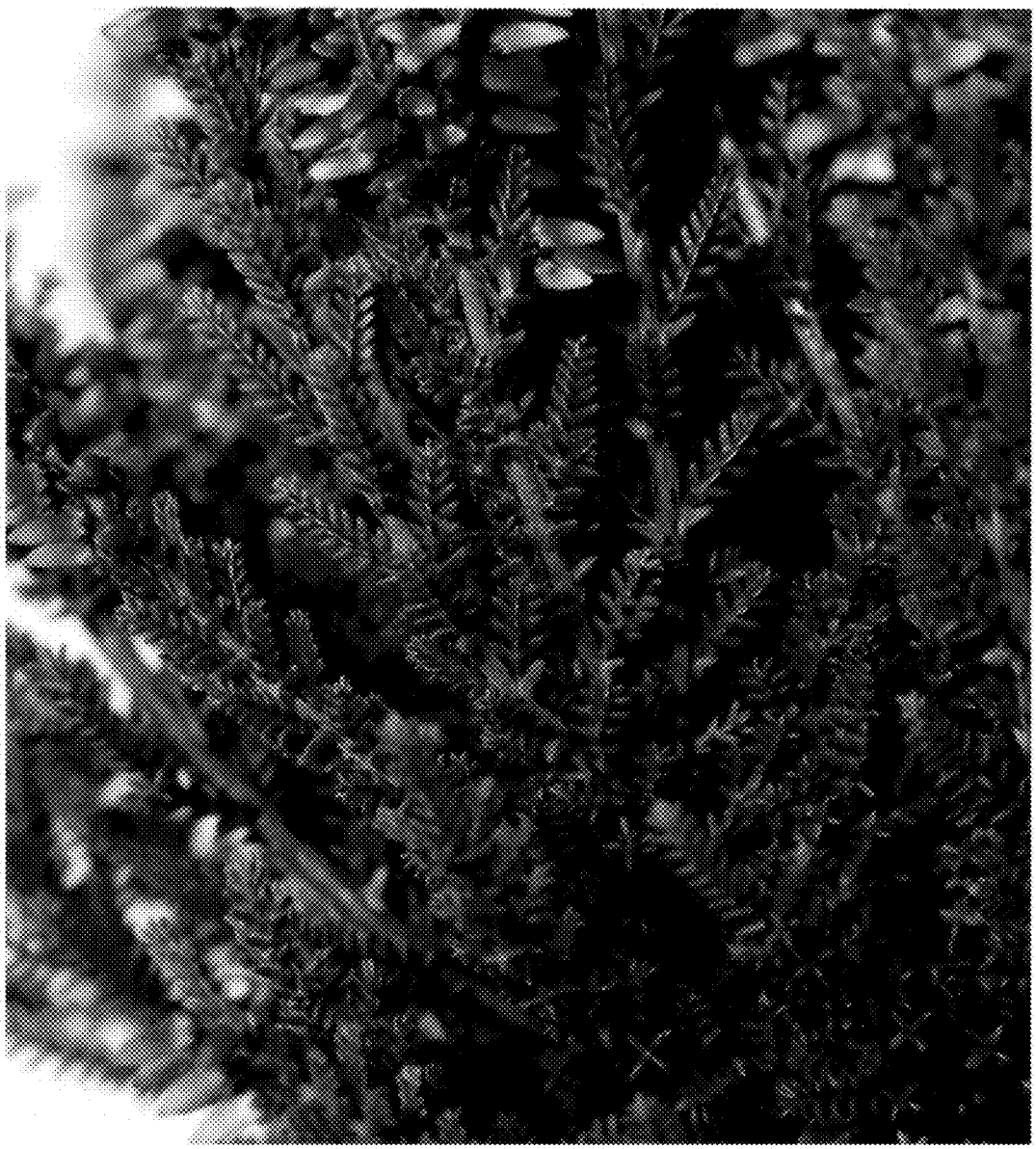

The photograph in FIG. 3 provides a close-up view of the foliage of 'Lynn'.

The colors in the photographs are as close as possible with the photographic and printing technology utilized and the color values cited in the detailed botanical description accurately describe the colors of the new *Calluna*.

DETAILED BOTANICAL DESCRIPTION

The following is a description of a 1-year-old plant as grown outdoors in 10-cm containers in Wezep, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—8 weeks from late September to mid-November in The Netherlands.

*Plant type.*—Evergreen shrub.

*Plant habit.*—Broadly spreading, upright, and densely branched.

*Height and spread.*—Average of 20.2 cm in height, (soil level to top of foliar plane), 24.6 cm in height (soil level to top of floral plane), 21.2 cm in diameter as a one-year-old plant in a container, a fully mature plant in the landscape reaches 50 cm in height and spread.

*Hardiness.*—At least in U.S.D.A. Zones 5 to 9.

*Diseases and pests.*—No resistance or susceptibility to diseases or pests has been observed.

*Root description.*—Fine.

*Propagation.*—Stem cuttings.

*Root development.*—Root initiation is 5 weeks, time to produce a young rooted plant is approximately 6 months.

*Growth rate.*—Moderately vigorous.

Branch description:

*Branch shape.*—Round.

*Branch strength.*—Strong.

*Branch color.*—Young; 183A, mature; 197A, older branches and bark; 200C to 200D.

*Branch size.*—Lateral branches are an average of 13.5 cm in length and 1.75 mm in diameter.

*Branch surface.*—Matte, densely covered with glandular pubescence; an average of 0.1 mm in length, 194C to 194D in color.

*Branch aspect.*—Held in an average angle of 30° to main branch.

*Internode length.*—Average of 5 mm.

*Branching.*—Freely branched from base with 12 main stems and 90 lateral branches per plant.

Foliage description:

*Leaf shape.*—Narrow ovate to narrow oblong.

*Leaf division.*—Simple.

*Leaf base.*—Cuneate.

*Leaf apex.*—Bluntly acute.

*Leaf fragrance.*—None.

*Leaf venation.*—Pinnate, main vein visible on lower surface, 138B to 138C.

*Leaf margins.*—Entire.

*Leaf arrangement.*—Opposite.

*Leaf attachment.*—Sessile.

*Leaf aspect.*—Triangular in cross-section, average angle of 45° to lateral branch.

*Leaf number.*—Average of 1,000 per lateral branch.

*Leaf surface.*—Smooth, slightly leathery, both surfaces non-rugose, very slightly glossy, upper surface and margins are sparsely covered with very short glandular hairs, 0.1 mm in length, thin and transparent hard to measure color.

*Leaf size.*—Average of 2 mm in length and 0.75 mm in width.

*Leaf color.*—Young upper surface; 143A, young lower surface; 143A, tinged 176A, mature upper and lower surface; 137A.

Inflorescence description:

*Flower type.*—Solitary, flower buds borne at the leaf-axils, flowers remain in the bud stage and do not open.

*Flower fragrance.*—None.

*Flower lastingness.*—Average of 1 month, persistent.

*Flower bud description.*—Ovate in shape, an average of 4 mm in length and 1.5 mm in width, surface is smooth, moderately glossy, and glabrous, 71A in color.

*Flower quantity.*—Average of 4,000 per plant.

*Flower density.*—Medium to dense.

*Flower aspect.*—Held outward to slightly drooping.

*Flower shape.*—Ovate.

*Flower size.*—An average of 1.75 mm in depth and 5 mm in diameter.

*Peduncles.*—Average of 1 mm in length, 0.5 mm in diameter, held in an average angle of 45°, surface is matte, smooth and glabrous, 183A in color.

*Pedicels.*—None.

*Calyx form.*—Rotate in form, average of 1 mm in length and 1.75 mm in diameter.

*Sepals.*—4, whorled, average of 1 mm in length, 0.8 mm in width, ovate in shape, margin entire and fimbriate hairs less than 0.2 mm in length, NN155A in color, apex is bluntly acute, cuneate and fused base, surface is smooth, matte, glabrous, both surfaces 137A in color.

*Petals.*—Do not open, remain in closed bud stage, only visible outer surface (lower side) smooth, glabrous, very slightly velvety, moderately glossy, color; young 70A, mature; a blend of 70B and 75A, top 75B.

Reproductive organs:

*Stamens.*—Flowers remain in bud form; therefore, no stamens were available for data collection.

*Pistils.*—Flowers remain in bud form; therefore, no pistils were available for data collection.

*Fruit and seed.*—None have been observed to form.

It is claimed:

1. A new and distinct cultivar of *Calluna* plant named 'Lynn' as herein illustrated and described.

* * * * *